United States Patent
Densert et al.

[11] Patent Number: 6,159,171
[45] Date of Patent: Dec. 12, 2000

[54] DEVICE FOR AFFECTING THE HYDRODYNAMIC SYSTEM OF THE INNER EAR

[75] Inventors: Barbara Densert; Ove Densert; Jörgen Jöholm; Carl Johan Hörberg, all of Halmstad, Sweden

[73] Assignee: Pascal Medical AB, Halmstad, Sweden

[21] Appl. No.: 09/091,724

[22] PCT Filed: Dec. 20, 1996

[86] PCT No.: PCT/SE96/01742

§ 371 Date: Jun. 22, 1998

§ 102(e) Date: Jun. 22, 1998

[87] PCT Pub. No.: WO97/23178

PCT Pub. Date: Jul. 3, 1997

[30] Foreign Application Priority Data

Dec. 22, 1995 [SE] Sweden .................................. 9504658

[51] Int. Cl.[7] .............................. A61H 23/00; A61B 5/12; A61B 5/03
[52] U.S. Cl. .............................................. 601/76; 600/559
[58] Field of Search ................................ 601/76, 77, 10; 600/559; 607/105

[56] References Cited

U.S. PATENT DOCUMENTS

| 2,652,048 | 9/1953 | Joers | 601/76 |
|---|---|---|---|
| 4,325,386 | 4/1982 | Katz | 600/559 |
| 4,466,438 | 8/1984 | Katz | 600/559 |
| 4,754,748 | 7/1988 | Antowski | 601/76 |
| 4,757,807 | 7/1988 | Densert et al. | 601/76 |
| 4,841,986 | 6/1989 | Marchbanks | 600/559 |
| 5,577,511 | 11/1996 | Killion | 600/559 |
| 5,811,681 | 9/1998 | Braun | 6090/559 |

FOREIGN PATENT DOCUMENTS

| 0266474 | of 0000 | European Pat. Off. |
|---|---|---|
| 8302556 | of 0000 | WIPO |
| 8601399 | of 0000 | WIPO |
| 9308775 | of 0000 | WIPO |
| 8302556 | 8/1983 | WIPO |
| 8601399 | 3/1986 | WIPO |

*Primary Examiner*—Paul J. Hirsch
*Attorney, Agent, or Firm*—Ostrolenk, Faber, Gerb & Soffen, LLP

[57] ABSTRACT

A device for affecting the hydrodynamic system of the internal ear, said system including the perilymph and the endolymph. A first apparatus generates a desired static-pressure level. A second apparatus varies the static-pressure level. A third connector between the first and second devices affects the static pressure level upon predetermined pressure changes in accordance with a predetermined program controlled by a control unit. The first device includes a medium pump for generating the desired static-pressure level in a medium reservoir. The second device includes a unit for causing movements of a membrane which is connected to the reservoir. These movements are arranged to cause variations of the static-pressure level. The membrane has a predetermined area, and the unit is arranged to affect the membrane by a force of a certain magnitude to generate the pressure changes.

12 Claims, 2 Drawing Sheets

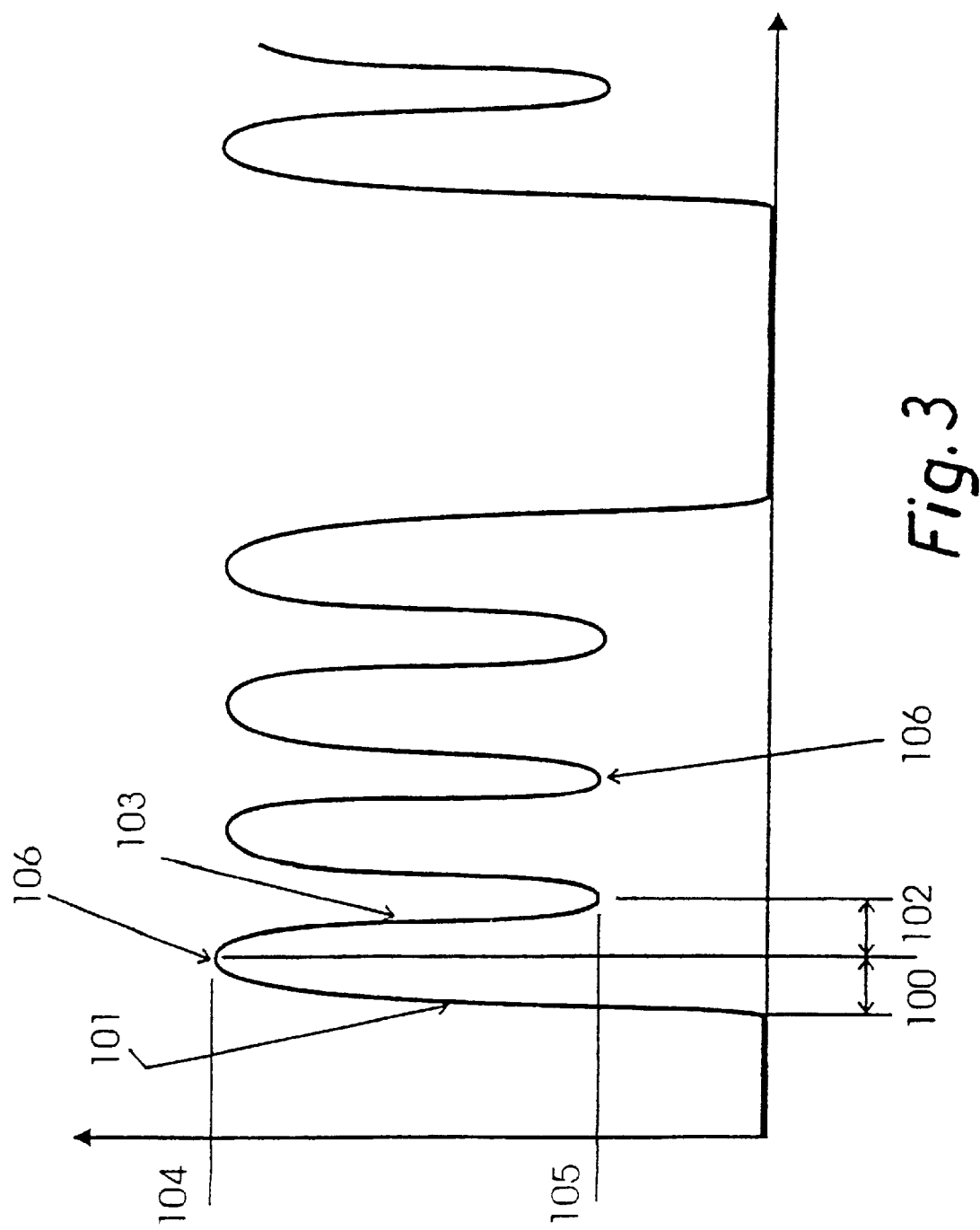

DEVICE FOR AFFECTING THE HYDRODYNAMIC SYSTEM OF THE INNER EAR

BACKGROUND OF THE INVENTION

The present invention relates to a device for affecting the hydro dynamic system of the inner ear, which system includes the paralymph and endolymph. The device may be utilized for instance in the treatment of patients suffering from the Ménière's disease, as described in U.S. Pat. No. 4,757,807 which is included herein by reference.

A device of the type outlined above is described e.g. in WO 83/02556. This device comprises a first means for generating a desired static-pressure level, a second means for causing a variation of the static-pressure level, a third means for connecting said first and said second means to the auditory tube, and a fourth means for interconnecting the auditory tube and the middle ear to facilitate transfer of the pressure changes generated in the auditory tube to the middle ear to affect the hydrodynamic system of the ear.

The first means preferably is an air pump in the form of a diaphragm pump having a membrane that is affected by a reciprocating piston for build-up of the static pressure in a reservoir.

The second means includes a unit adapted to produce the movements of a membrane part which is connected to the reservoir, said movements designed to produce the variations of the static-pressure level.

In this device the movements of the membrane part of the second means are produced manually or by means of a second piston, which is connected to the membrane part and which by means of an eccenter device is arranged to be displaced by certain distance and in doing so displace the membrane part. It has proved to be important that the generated pressure pulses follow a certain predetermined configuration as closely as possible in order to provide maximum treatment results, it thus becoming possible to vary the configuration of the pressure pulses from one person to the next and from one treatment to the other. This prior-art device does not, however allow comparisons to be made between a generated pressure pulse and a desired pressure pulse, for which reason it is impossible to regulate the pumping effect in accordance with the configuration of the generated pressure pulses in order to obtain the desired pressure pulses. In order to adapt the configuration of the pressure pulses to a certain treatment or to a certain person some manual adjustment may, however, be effected. For instance, it is possible to replace the eccenter means. However, this is an inconvenient and time-consuming operation. Since the membrane part in accordance with one embodiment is displaced by a certain distance by an eccenter means, it is not either certain that the adequate pressure pulses are generated in the device, since it may be necessary to vary the distance, for example to compensate for certain leakage as may occur in the device or between the device and the ear.

It is medically proven that negative pressure (depression) in static form as well as in the form of infrasound are harmful to the ear. In the prior art device pumping movements may, at least initially, cause a negative pressure to be generated in the ear. This may happen for instance when a pumping movement starts by a suction stroke. Also, if for instance a valve means, such as non-return valve, is provided through which air is sucked into the device during the suction stroke, a certain depression may nonetheless be generated in the ear during the suction stroke.

WO 93/08775 discloses another device of the above-mentioned type. This device comprises a housing, a membrane disposed in the housing, and means for actuating the membrane. The membrane and the housing form a chamber which is connected to the ear by means of connection means. Pressure pulses are generated as the membrane is displaced by said means. The means includes a piston which is connected to the membrane. The piston is displaced by an electric motor. In order to create a static pressure the membrane is displaced by the piston by a predetermined distance in a first direction to a biased position around which the membrane is displaced to generate the pressure pulses. The device also includes a pressure-sending means adjacent to the connection means, which sensing means is connected to a control unit. When the static pressure is reduced, for instance on account of leaks at the ear, a signal generated by the pressure sensing mean is supplied to the control unit which in turn emits a signal to the membrane for displacement of the piston in the first direction to a new biased position, said displacement reducing the size of the chamber. A disadvantage inherent in this arrangement is that the dimensions of the chamber may become so small immediately or after several such displacements that the treatment must be interrupted to allow the chamber size to be increased once more by displacement of the membrane in the other, the opposite direction, whereupon a new static pressure must be built up. In addition, advanced control of the device is necessary in order to generate the desired pulses, with the result that the device has an expensive and complicated construction. Also in this device the pressure pulses are generated by displacement of the piston by a predetermined distance, which distance does not always produce the same pressure changes in the device, which is due, among other things, to the leakage variations between the device and the ear, resulting in unnecessary adjustments from the control unit that governs the piston displacements.

Also in the case of this device a pumping movement may, at least initially, produce a negative pressure in the ear, should the pumping movement start by a suction stroke, since a certain resistance against air through-flow always exist across the non-return valve that is connected to the chamber.

Generally speaking, the prior art solutions are deficient with respect to the control and the regulation of the pulses, leading to highly varying treatment results are in some cases negative ones. In addition, the prior art solutions produce a comparatively high level of noise, which the patient may find unpleasant and which in some cases may even be detrimental and thus negatively affect the treatment results.

SUMMARY OF THE INVENTION

One object of the present invention is to provide a device for affecting the hydrodynamic system of the inner ear, which device eliminates the above-mentioned drawbacks, has a simple and inexpensive construction and is safe and efficient to use. These and other objects are obtained in accordance with the present invention by means of a device designed to affect the hydrodynamic system of the internal ear.

BRIEF DESCRIPTION OF THE DRAWINGS

In the drawings:

FIG. 3 is a schematic graph of the time curve for the pressure when using the device in accordance with FIG. 1.

DETAILED DESCRIPTION OF THE PREFERRED EMBODIMENT

Figure 1:
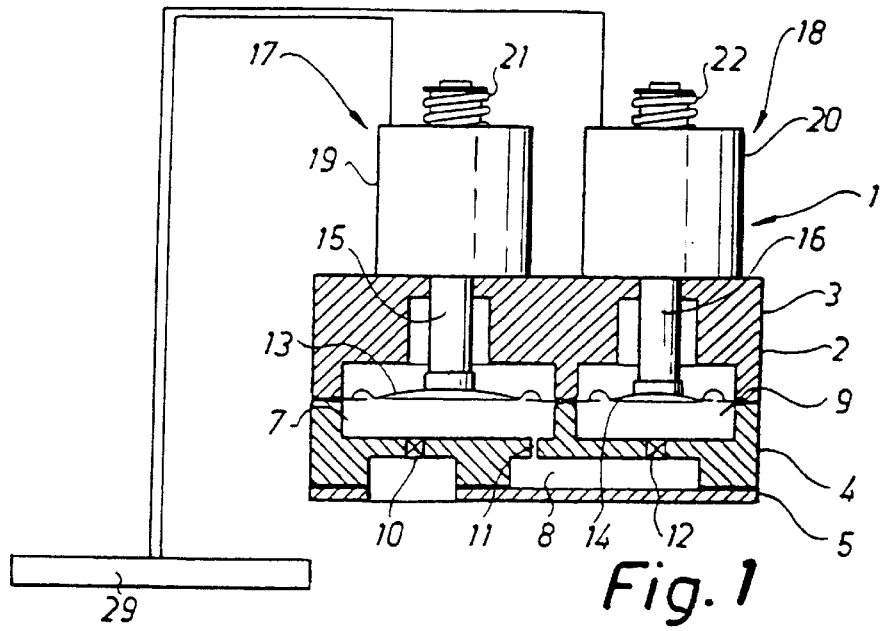
FIG. 1 is a cross-sectional schematical lateral view of one embodiment of the present invention.
Figure 2:
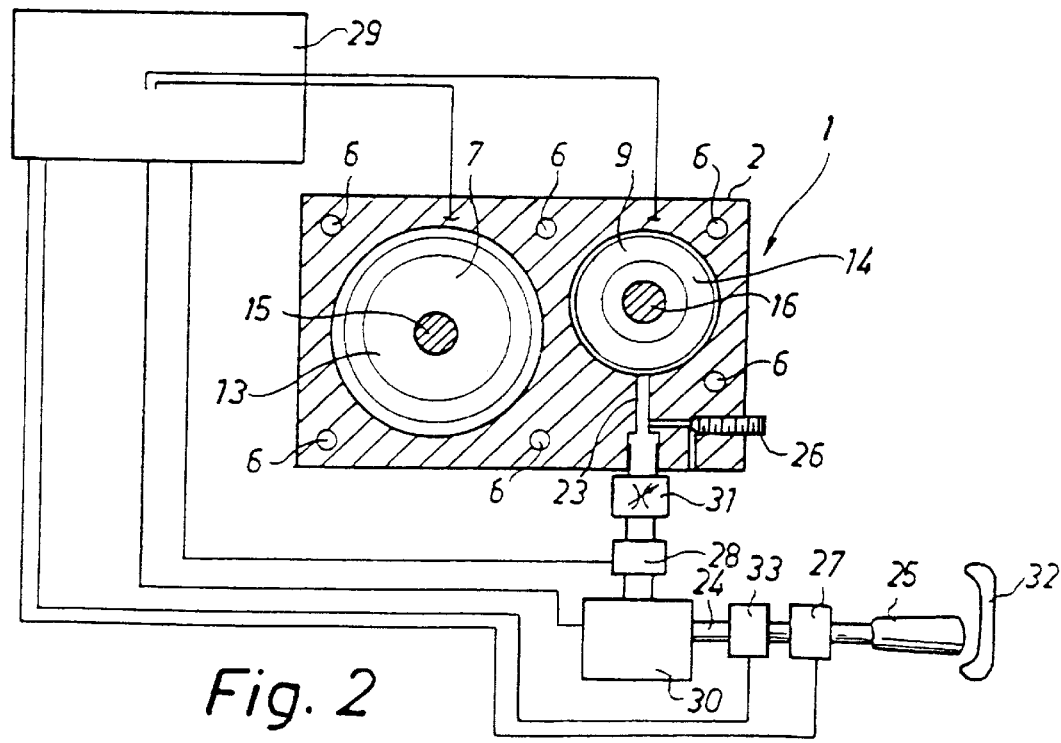
FIG. 2 is a schematically cross-sectional view as seen from above, of the embodiment of FIG. 1.

The invention device, generally designated by 1, comprises a housing 2 which in accordance with the embodiment illustrated has an upper part 3, an intermediate part 4, and a lower part 5, said parts being interconnected by means of e.g. fastening means (not shown) located in apertures 6. In accordance with the embodiment illustrated, the housing 2 comprises a first chamber 7, a second chamber 8, and a third chamber 9. A non-return valve 10 communicates the first chamber 7 with the environment and a chamber 11 interconnects the first chamber and the second chamber 8, the latter in turn being connected to the third chamber 9 via a non-return valve 12.

The chambers 7 and 9 are formed with one membrane each, 13 and 14, respectively, which membranes sealingly partition the chambers into one upper and one lower part. Pistons 15 and 16 connect the respective membrane 13, 14 with their respective one of electromagnet units, generally designated by 17 and 18, respectively. Each electromagnet unit 17, 18 comprises an electromagnet, 19 and 20, respectively, and a return spring, 21 and 22 respectively. Owing to the provision of the electromagnets the pistons may be operated practically inaudibly.

Sound of a predetermined frequency and amplitude may be supplied at predetermined times by a means 27, which in certain cases may facilitate the transmission of the pressure from the middle ear to the interior ear, a feature having a positive effect on the treatment.

The lower part of the third chamber 9 communicates with an interconnection means, for instance in the form of a channel 23, to which a hose 24 and a nozzle means 25 are connected. The channel 23 may also be provided with some kind of leakage arrangement, for instance in the shape of a needle valve means 26.

The device 1 may comprise a unit 27 generating sonar pulses and being positioned e.g. adjacent the interconnection means. In addition, the device in accordance with the embodiment illustrated comprises a pressure sensor 28 which is connected with a control unit 29, in turn connected to the electromagnets 19 and 20. Furthermore, the device comprises a safety transducer 30 which is connected to the control unit 29. The device likewise comprises a throttle valve 31.

The control unit 29 comprises means for controlling the waveform illustrated in FIG. 3, for instance with respect to the rise time 100 and the rise function 101 (i.e. the change of the derivative over the rise time), the fall time 102 and the fall function 103 (i.e. the change of the derivative over the fall time), the pressure maximum values 104, the pressure minimum values 105, and the total amount of positive pressure, i.e. the integral of the pressure-time function. The rise functions and the fall functions could for example be linear, exponential or follow some other mathematical function. The control means may also comprise the transition area 106 between the rise function and fall function and the fall function and rise function, respectively, i.e. if the transition occurs abruptly, which generates a pointed waveform or gradually over a certain period, which produces a rounded waveform. The maximum values 104 may be the same for all pulse peaks or differ, depending on the order of the pulses, and the same is true with respect to the rise times 100 and the fall times 102. More particularly, the first rise time in a series of pulses may differ from the rest, as also the end fall time. The control of these variables in a correct and controlled manner is of decisive importance to the success of the treatments for which the device in accordance with the invention is used. Pressure pulses that are sufficiently controlled by these factors but have equivalent values with respect to pressure and amplitude could, instead of improving, even cause deterioration in the patient being treated. The pressure supplied to the ear must be adapted to the built-in, natural ability of the ear to adapt to pressure in order to have a favourable effect on the ear. This ability could vary highly from individual to individual on account of the dimensions and the permeability of the cavities, membranes and vessels through which the ear functionally communicates with the circulatory system and the cerebrospinal fluid system.

In addition, the volume of the middle ear and other transmission characteristics may vary considerably from one individual to the next. Thus, the control unit compensates for the effects of the middle ear on the predetermined waveform that is wall adapted to the inner ear. Previous clinical and experimental experience shows that it is important for successful treatment results that the pressure pulses are transferred to the inner-ear fluids substantially independently of the volume and transmission characteristics of the middle ear.

The control unit in accordance with the invention furthermore preferably is arranged to compensate for external circumstances, such as air pressure variations, fluctuating voltage levels and so on, to ensure that the desired pulse configuration is obtained and maintained, irrespective of the environment.

In addition, the control unit 29 may be connected to a meter of some kind, in order to obtain feed back for improved control. Such meters may for instance be sensors for sensing the pressure generated by the device. The measurement means could also be stimulus sensing means which through so called electrocochleography or in any other suitable manner measure the effects of the treatment in the ear. Such measurements may be effected prior to and after the pressure pulse treatment or continuously while the treatment is in progress.

The data derived from the sending of the voltage across the electromagnets 19, 20 and possibly also from the sensing of the positions of the pistons 15, 16 may be used for feed back control. Data from the sensing may also be used to indirectly calculate the output pressure.

The device functions as described in the following. A control unit 29, which could for instance be a microprocessor, is supplied with the desired data represent-static pressure level during the pressure-pulse generation. In this case it is, however, essential that the static pressure level does not increase but that the control unit 29 regulates the pumping motion in such a manner that the static pressure level essentially coincides with the predetermined level.

The membrane 14, the piston 16 and the electromagnet unit 18 are arranged to cause variations of the static pressure level in the lower part of the chamber 9, and thus of the static pressure level in the middle ear. When the piston 16, being influenced by the electromagnet unit 18, is moved in a reciprocating motion according to certain predetermined program that has been stored in the control unit 29, this motion causes the membrane 14 to move correspondingly, which generates pressure pulses. The pressure pulses are registered by the pressure sensing means 28, and the control unit 29 is arranged to regulate the effects of the electromagnet 20 on the piston 16 to ensure that the generated pressure pulses coincide with the desired pressure pulses as far as possible.

When the inventive device 1 is used, normally a first series of pressure pulses is generated, whereafter the pressure in the middle ear may be reduced, whereupon a second series of pressure pulses is generated, and so on. The leakage arrangement 26 is arranged to cause the pressure reduction in between these series of pulses. The leakage arrangement 26 is adjustable to provide the correct pressure drop in between the pulse series. It is understood that the leakage means 26 could also be controlled by the control unit 29 (not shown), in order to provide the desired pressure reduction in between the pulse series. The control unit 29 may also be given a function regulating the intervals between the pressure pulse series.

Thus, the control unit 29 may be arranged to control an entire sequence of pressure pulse series, and the tive of configuration, frequency and amplitude of the pressure pulses to be generated by the device. The nozzle piece 25 is inserted into the auditory tube of the ear 32. In turn, the auditory tube is connected to the middle ear, e.g. via a tube in the tympanic membrane. In operation of the device, an upwards-downwards movement of the piston 15 is achieved by electrical actuation thereof from the electromagnet 19 in combination with a force excerted by the return spring 21. The electromagnet 19 displaces the piston 15 downwards as seen in FIG. 1, and the return spring 21 moves the piston 15 upwards, imparting to the membrane 13 an upwards-downwards pumping motion, the medium, in this case air, being sucked into the lower part of the chamber 7 via the non-return valve 10 and displaced into the chamber 8 and further, past the non-return valve 12, to the lower part of the chamber 9 and into the interconnection means and from there into the middle ear via the auditory tube. Since the area intermediate the nozzle 25 and the ear is essentially sealed, a static pressure is built up inside the chamber 9 and consequently in the middle ear. The static pressure is registered by the pressure sensing means 28 and is transferred to the control unit 29 which in turn, in accordance with one embodiment, interrupts the pumping motion of the static-pressure generating means when a predetermined treatment pressure level is obtained. It is easily understood that the pumping motion of the static-pressure generating means may be re-started by the registers a drop in the static pressure below a predetermined pressure level. It is also easily understood that the pumping motion of the static-pressure generating means need not be interrupted when the predetermined static pressure level has been obtained. Instead, the pumping motions may be maintained by the control unit 29, preferably with less intensity, in order to ensure that the pressure level does not fall below the predetermined pressure pulse series may be given different configurations depending on the order in which they appear. Should for instance the pressure sensor means 28 fail for some reason and a non-desired high pressure build up in the interconnection means, the safety sensor means 30 is arranged to emit the signal to the control unit 29, the latter in turn being arranged to cease the pressure-raising movements of the pistons 15 and 16. When a leakage means 26 is provided adjacent to the lower part of the chamber 9 or adjacent to the connection means, further pressure reduction may occur in addition to the pressure reduction that may occur through leakage between the nozzle part 25 and the ear 32.

The throttle valve 31 is arranged to level out the configuration of the generated pressure pulses and thus it also serves as an additional safety means, should unexpectedly large pressure variation be generated by the device 1.

In accordance with the embodiment illustrated the pressure-raising piston strokes are produced by the electromagnets 19 and 20, respectively. The return movements of the pistons 15, 16 are produced by the return springs 21 and 22, respectively. In the starting position, no voltage is applied across the electromagnets 19 and 20, respectively, and the pistons 15 and 16, actuated by the return springs 21, 22 respectively, then assume the retracted position. When the pressure generation is initiated in the device 1, a pressure-raising piston stroke is first produced in the device 1 as a result of the electromagnets 19 and 20, respectively, causing displacement initially of piston 15 and then piston 16. Owing to this construction no negative pressure (depression) in static form or in the form of negative pressure pulses may be generated in the device. This is a technical effect which cannot with certainty be obtained in the prior-art constructions.

Preferably, the medium, which preferably is air, reaching the ear of the patient is essentially at body temperature, i.e. approximately +37° C., since vertigo may be induced, should the temperature of the medium deviate from this temperature. In accordance with a preferred embodiment the device 1 therefore is equipped with a heating device 33 arranged to heat the medium inside the device 1. In accordance with a preferred embodiment the heating device 33 has a temperature transducer and it is connected to the control unit 29. In this respect, the control unit 29 is arranged to regulate the temperature of the medium reaching the ear with the aid of the heating device 33. In accordance with one embodiment, the device 1 is thermally insulated (not illustrated), in order to increase the possibility of maintaining the temperature of the heated medium at the desired level. It is easily understood that the heating device 33 in accordance with one embodiment may also be used to cool the medium, should it have a temperature exceeding that of the body temperature. In accordance with this embodiment insulation of the device 1 may also be used to increase the possibility of maintaining the temperature of the cooled medium.

In accordance with a simpler version, the device is likewise provided with a temperature transducer, which may be connected to e.g. the control unit 29. A switch, controlled by the temperature transducer, may be provided, making the device usable only at certain temperature levels. This arrangement prevents use of the device outside the predetermined temperature range, i.e. when it is too warm and/or too cold.

Contrary to the situation in prior-art technology, the control of the displacement of the pistons 15, 16 does not depend on a certain distance of displacement. Instead, the displacement of the pistons depends on a force of predetermined magnitude applied on the pistons 15, 16 and thus on the membranes 13 and 14 by the electromagnet units 17 and 18, respectively. Since the membranes 13, 14 have a predetermined area, a predetermined force excerted on the membranes 13, 14 results in a predetermined pressure being generated in the device, which provides a more exact pressure generation than in accordance with the prior art technology. Since the displacement of the pistons 15, 16 is the result of the magnitude of the force applied thereon and since the volume of the middle ear of the patients vary, the pressure generation is adapted to the volume of the middle ear of the patient being treated. This being the case, a serious technical problem has been solved compared with prior-art technical solutions. Because the displacement of the pistons 15, 16 is force-induced a further safety feature is obtained, since in the case of too high pressures in the device 1 a more powerful force is required to displace the pistons 15, 16 and consequently they cannot be displaced to the same extent as when a lower pressure resides in the device 1. The feed back to the control unit 29 via the pressure sensor means 28 and the safety sensor means 30 and the provision of the throttle valve 31 increase the safety of the device further. Since the displacement of the pistons 15, 16 is force-induced the pressure pulse generation need not be regulated to the same extent as for instance in accordance with the device disclosed in WO 93/08775, for which reason the control equipment used in the inventive device may be comparatively simple and inexpensive. Because the electromagnet units 17, 18 are used for the force-induced displacement of the pistons 15, 16 an essentially continuous variation of the force applied on the pistons 15, 16 becomes possible, a feature which additionally increases the possibilities of generating the desired pressure pulses.

As is easily understood, it is possible to deviate somewhat from the embodiment described above. For instance, the unit 27 and the throttle valve 31 are not essential to the basic function of the device 1. In addition, the throttle valve 31 may be replaced for instance by a means providing the corresponding function by electric means. Further, the electromagnet units 17, 18 may be replaced by other means that are able to actuate movable means 15, 16 by a certain force. For instance, electromagnets may be used to cause the means 15, 16 to move in both directions. It is also understood that the number of the chambers 7, 8, 9 may be varied. For instance, only one chamber and one piston may be used, it being possible to obtain the pressure variations by means of a variable leakage valve. All varieties and modifications comprised by the basic inventive idea thus should be regarded to be included in the appended claims.

We claim:

1. A device for affecting the hydrodynamic system of the internal ear which system includes the paralymph and the endolymph, the device comprising:

a body;

a pressure generator disposed in the body, the pressure generator operable for generating a desired static pressure level in the body, the pressure generator comprising:

a pressure varier for causing variation in the static pressure level in the body, a medium reservoir for containing a medium, a medium pump for generating the desired static pressure level of the medium in the medium reservoir, a first membrane connected with the medium reservoir such that deflection of the first membrane changes the static pressure level in the medium reservoir, and a first operator connected with the first membrane for deflecting the first membrane in the medium reservoir to cause the variations of the static pressure level in the medium reservoir;

a connection from the body to the internal ear for transferring pressure changes generated by the pressure generator;

a control unit connected with the pressure generator and including a predetermined program adapted to affect the static pressure level in the body by causing predetermined pressure changes in the body of the static pressure level provided by the pressure generator, the control unit including a program for controlling at least some parameters of the static pressure level in the body, the parameters including rise time, rise function which is the variation of the derivative for the duration of the fall time, appearance of the transition from the rise function to the fall function and from the fall function to the rise function, maximum pressure values, minimum pressure values, and the total amount of positive pressure which is the integral of the function of pressure-time.

2. The device of claim 1, wherein the first membrane has a predetermined first area selected for achieving a particular pressure level in the medium reservoir and the first operator being connected with the first membrane for controlling deflection thereof by a force of predetermined magnitude to cause predetermined pressure variations in the static pressure.

3. The device of claim 1, wherein the connection connects the medium reservoir to the auditory tube of the internal ear.

4. The device of claim 1, wherein the medium pump includes a second deflectable membrane connected to the medium reservoir such that deflection of the second membrane pumps medium to the medium reservoir; the pressure generator being connected with the second membrane for causing the second membrane to apply a force of predetermined magnitude to the medium in the medium reservoir to produce the static pressure level, and the static pressure level is varied by the first membrane.

5. The device of claim 4, wherein the pressure generator further comprises a second membrane operator connected to the second membrane for deflecting the second membrane.

6. The device of claim 5, further comprising a respective first and second electromagnet connected respectively with the first and second operators such that operation of each electromagnet moves the respective operator.

7. The device of claim 6, further comprising a respective first and second spring operating on each of the first and second operators in opposition to the movements on the operators due to operations of the first and second electromagnets, whereby the opposing action of the first electromagnet and the first spring and the opposing action of the second electromagnet and the second spring deflects the first and second membranes respectively to generate and to affect the static pressure level in the body.

8. The device of claim 7, wherein each of the first and second electromagnets is operable to displace the respective first and second operator with a force of predetermined magnitude in a pressure increasing direction, and each of the first and second springs is a return spring operable to move the respective first and second operator in the opposite not pressure increasing direction.

9. The device of claim 1, further comprising a pressure sensor connected with connection from the body and with the control unit for regulating the pressure pulses generated in the medium reservoir.

10. The device of claim 9, further comprising a safety sensor connected to the connection and to the control unit for measuring the pressure supply to the connection, the safety sensor being operable to operate the control unit for interrupting pressure generation by at least one of the pressure generator and the control unit when the safety sensor registers a predetermined pressure at the connection.

11. The device of claim 1, wherein the control unit is programmed for controlling an entire sequence of a series of pressure pulses in the body when the pressure pulses are configured selectively dependent upon their sequential order.

12. The device of claim 1, further comprising means adapted to prevent its use outside a predetermined temperature range of the medium.

* * * * *